United States Patent
Howe et al.

(10) Patent No.: US 6,800,246 B2
(45) Date of Patent: Oct. 5, 2004

(54) BULK DECONTAMINATION AND DEGERMINATION OF MATERIALS IN A SUB-ATMOSPHERIC SATURATED STEAM ENVIRONMENT

(75) Inventors: David Howe, Newport, RI (US); Michael Howe, Newport, RI (US); Marek Janasek, Warren, NJ (US)

(73) Assignee: Cosmed Group, Inc., Jamestown, RI (US)

(*) Notice: Subject to any disclaimer, the term of this patent is extended or adjusted under 35 U.S.C. 154(b) by 118 days.

(21) Appl. No.: 10/298,643

(22) Filed: Nov. 19, 2002

(65) Prior Publication Data

US 2003/0118471 A1 Jun. 26, 2003

Related U.S. Application Data

(60) Provisional application No. 60/331,519, filed on Nov. 19, 2001.

(51) Int. Cl.[7] .................................................. A61L 2/00
(52) U.S. Cl. ......................... 422/26; 422/37; 422/298; 422/299; 422/305; 422/307
(58) Field of Search .......................... 422/26, 37, 298, 422/299, 305, 307

(56) References Cited

U.S. PATENT DOCUMENTS

| | | |
|---|---|---|
| 4,164,538 A | 8/1979 | Young et al. |
| 4,203,947 A | 5/1980 | Young et al. |
| 4,261,950 A | 4/1981 | Bainbridge et al. |
| 4,263,258 A | 4/1981 | Kalasek |
| 4,309,381 A | 1/1982 | Chamberlain et al. |
| 4,372,916 A | 2/1983 | Chamberlain et al. |
| 4,637,916 A | 1/1987 | Hennebert et al. |
| 4,687,635 A | 8/1987 | Kaehler et al. |
| 4,759,909 A | 7/1988 | Joslyn |
| 4,761,009 A | 8/1988 | Gibree |
| 4,808,377 A | 2/1989 | Childers et al. |
| 4,844,933 A | 7/1989 | Hsieh et al. |
| 5,344,609 A | 9/1994 | Long |
| 5,424,046 A | 6/1995 | Smith et al. |
| 5,500,238 A | 3/1996 | Thienpont |
| 5,523,053 A | 6/1996 | Dudek |
| 5,615,518 A | 4/1997 | Suzuki et al. |
| 5,759,488 A | 6/1998 | Eser et al. |
| 5,906,800 A | 5/1999 | Napierkowski et al. |
| 5,997,813 A | 12/1999 | Yaskoff et al. |
| 6,153,240 A | 11/2000 | Tottenham et al. |
| 6,264,889 B1 | 7/2001 | Tottenham et al. |

FOREIGN PATENT DOCUMENTS

| | | |
|---|---|---|
| EP | 0006369 | 1/1980 |
| FR | 2635167 | 2/1990 |

*Primary Examiner*—Krisanne Jastrzab
(74) *Attorney, Agent, or Firm*—Patton Boggs LLP

(57) ABSTRACT

A method and apparatus for significantly reducing the biological load on consumer products such as food products, spices, produce, botanicals, cosmetic ingredients, barrels, pallets, crates, birdseed and medical products is disclosed. The method involves applying a continuous stream of saturated steam to a material in a sealed biological burden reduction chamber. The continuous stream of saturated steam is created in said chamber by correlating a desired temperature to pressure based on the use of Saturated Steam Tables. The apparatus includes: (a) a bioburden reduction chamber; (b) a temperature controller; (c) an air injection system; (d) a steam injection system; and (e) an evacuation system.

10 Claims, 3 Drawing Sheets

BULK DECONTAMINATION AND DEGERMINATION OF MATERIALS IN A SUB-ATMOSPHERIC SATURATED STEAM ENVIRONMENT

CROSS REFERENCE

This application claims priority to U.S. provisional application Ser. No. 60/331,519, filed Nov. 19, 2001, the entire contents of which are incorporated herein by reference.

FIELD OF THE INVENTION

The present invention generally relates to a method and apparatus that can be utilized to significantly reduce the biological load such as bacteria, insects and noxious weeds (bioburden) from consumer products such as produce, foods, spices, bird feed, botanicals, cosmetics and medical products. These products have traditionally been treated with commercial sterilants or fumigants such as ethylene oxide, propylene oxide, methyl bromide, hydrogen phosphide, high heat, irradiation, and the like. Other material, such as packaging, wood barrels and wood pallets, may also benefit from the invention disclosed herein. The method and apparatus, which involve the use of sub-atmospheric saturated steam, provide advantages in bulk processing of target materials while minimizing product quality loss.

BACKGROUND OF THE INVENTION

For many years, food products such as spices and leafy herbs have been sterilized using ethylene oxide. This process is inexpensive and is applied to bulk loads of material. Palletized products are loaded into a chamber and the door of the chamber is sealed. The process is performed by removing air, injecting the sterilant gas, waiting for a predetermined exposure period and then removing the gas. Ethylene oxide is a suspected carcinogen and is highly flammable. Most recently, continuing regulatory pressure on ethylene oxide processing has caused manufacturers to investigate alternative technologies.

For example, U.S. Pat. No. 4,844,933 discloses a method for steam treating spices in a series of chambers and pneumatically conveying the spices between the chambers. This system is suitable for unpackaged spices that are physically capable of pneumatic conveyance through the system.

U.S. Pat. No. 5,344,609 discloses a method for gradually heating steam treated products to prevent flashing related damage. This process involves incremental pulses of steam in a series of chambers outfitted with steam injectors to carefully heat the product and kill the target organisms.

U.S. Pat. No. 5,523,053 discloses a method for steam treating spices in a series of chambers that relies on gravity for a means of conveyance between the chambers. The patent discloses the use of multiple chambers for a more uniform treatment process and the use of gravity to minimize the contamination of the treatment chamber to facilitate clean up between cycles.

U.S. Pat. No. 5,500,238 discloses a method for preserving foodstuffs. The method involves moving the foodstuffs in a pre-defined direction in a chamber and subjecting the foodstuffs to a flow of steam in a direction opposite to the direction of travel of the foodstuffs.

Each of these patents are variations on a theme. Each requires that the food product be removed from its packaging and introduced into a conveyance system. The system moves the product into a heated chamber that may or may not tumble the product. The size of the chamber is sufficiently small to allow for rapid heating of the entire load. Steam is injected into this tumbling chamber to increase product temperature. When the exposure time is sufficient to effect sterilization, the product is conveyed to a second chamber where the product is rapidly cooled and dried. From there the product is moved for further processing or repackaging.

These systems share many disadvantages and have not been used widely. Removing the packaging from the product is only cost effective when the products are sterilized at the manufacturing site. This is not typical handling for the industry. Many food products such as spices, particularly imported spices, are sterilized when a company that specializes in importing receives them. The importer verifies product quality, including bacteria and insect bioburden, and then sells the products based on those characteristics. By decreasing bioburden, sterilization increases product value. This step occurs before the manufacturer purchases the product. It is not possible in many cases to improve product quality prior to sale using techniques that require the removal of the packaging.

Conveyors for food products such as spices are designed for specific flow characteristics of the product. Powders, leaves and seeds are conveyed using different systems. A continuous flow sterilizer can only process products that are suitable for its conveyance systems. For example, powdered spices will tend to clump, which tends to inhibit flow. The conveyance systems also create the problem of line clearance and cleaning. It is often difficult to fully clear a conveyance line prior to beginning a batch of a new spice. In most cases these sterilizers are used for only one kind of spice or herb to avoid line clearing and cleaning issues.

U.S. Pat. Nos. 6,153,240 and 6,264,889 disclose an apparatus and method for microbial intervention of food and food processing equipment. The apparatus and method include application of steam for a controlled time period and subsequent application of chilled water to the food or food processing equipment.

U.S. Pat. No. 5,615,518 discloses a method for sterilizing seeds. The method involves exposing the seeds to dry heat, e.g., heated air or combustion exhaust gases, or wet heat, e.g., hot water.

U.S. Pat. No. 5,997,813 discloses a retrofitted steam sterilizer and use thereof. The retrofitted steam sterilizer provides savings in water supply and keeps the water cool. The patent does not disclose or suggest a particular sterilization methodology for the steam sterilizer.

FR 2635167 discloses a method and apparatus for sterilizing food or other products using steam. The method and apparatus function as a boiling apparatus that works under pressure or partial vacuum.

EP 0006369 discloses a method for heat treatment for precooking, pasteurization, sterilization, and blanching of bulk unwrapped, pre-packed or packed products. The method involves placing the products in a container, the walls of which have been prior heated to a specific temperature that is higher than the temperature that will be applied to the products. This method, however, was not directed to operate under the saturated steam pressure to prevent undesirable water loss during the treatment to ensure the quality of the products being pasteurized or sterilized.

U.S. Pat. No. 4,761,009 discloses a method and apparatus for steam sterilization in which goods are conditioned by removing air and heated to a desired temperature in a chamber. The goods are subjected to a plurality of pressure pulses at above atmospheric pressure by alternate pressurization and venting of the chamber to atmospheric pressure.

None of the cited references disclose a process that would enable products sensitive to harsh conditions to be treated as is or in packaging. Thus, a means to reduce undesirable and deleterious treatment of consumer products remains a necessity.

The present invention combines the advantages of prior technologies with improvements that address the disadvantages discussed. The product can be held in its original packaging. The process equipment can accommodate different food products without extensive line clearing and cleaning procedures. In fact, multiple food products can be processed simultaneously.

The process has the advantage of eliminating the viability of noxious weed seeds found as contaminants in bags of spice and bird feed. It is known that spices from foreign countries contain weeds which are not indigenous to the United States. If a population of these weeds was established inadvertently through the import of spices, domestic agriculture and native plant populations would be threatened. This process prevents the germination of these seeds.

Wooden pallets, crates and other wood packaging involved in the import of materials internationally are frequently infested by insects which could potentially harm native United States species. This process eliminates those insects.

Wooden barrels in the wine manufacturing industry are discarded after one use to prevent cross contamination from unwanted bacteria between batches. This process can eliminate those bacteria and render the barrels acceptable for reuse.

SUMMARY OF THE INVENTION

It is desirable to treat a wide variety of consumer products in chamber type operations in a cost effective manner. The method and apparatus of the present invention permit decontamination (hereinafter referred to as "bioburden reduction") of a product as is or in a container (e.g., burlap bag, fiber drum, kraft paper bag, plastic bag, etc.)). Packaging materials themselves benefit from this invention; pallets crates and barrels with undesirable contamination can be salvaged with this process. Thus, double handling, product loss, and post treatment contamination are reduced.

Accordingly, it is an object of the present invention to provide a method and apparatus for reducing bioburden from consumer products and packaging.

It is another object of the present invention to provide a method and apparatus for reducing bioburden on consumer products and packaging in a safe manner.

It is thus an object of the present invention to eliminate the health risks that are associated with the reduction of bioburden from consumer products and packaging.

It is a further object of the present invention to provide a simple, efficient and economical method and apparatus for reducing bioburden from consumer products and packaging that can be used at the site of production and/or packaging of such products.

In accordance with the above and other objects, the present invention is a method and apparatus for treating spices, produce, foods, packaging materials, bird feed, wooden barrels and wooden pallets to reduce bioburden. The method includes:

a. placing a material to be treated into a chamber;

b. selecting a desired temperature T1, wherein said desired temperature T1 is based on the material being treated;

c. determining a target pressure P1, wherein said target pressure P1 provides a saturated steam environment in said chamber at said desired temperature T1;

d. creating a vacuum in said chamber;

e. introducing steam into said chamber until the pressure is equal to said target pressure P1, thus indicating that said chamber has reached said target temperature T1; and f. maintaining the chamber at said temperature T1 and pressure P1 for a period time sufficient for said bioburden reduction. The apparatus includes: (a) a bioburden reduction chamber; (b) a temperature monitor and controller; (c) a pressure monitor and controller; (d) a steam injection system; and (e) an evacuation system.

According to another embodiment, the method is carried out as above except that prior to step e., the following steps are conducted to pre-heat a product that may be sensitive to rapid rise in temperature as follows:

d.1. steam to a pressure P1a lower than the final target P1 pressure is introduced until the product temperature is uniformly heated to T1a and the air is removed from the chamber. The process then proceeds as described above.

The bioburden reduction process of the invention replaces conventional chemical agents and solvents with steam to avoid any potential hazard associated with the use of chemical agents and solvents. The invention which does not require the use of a conveyance system provides improvements that enable the processing of target material in its original packaging. In addition, the process equipment can accommodate different food products without extensive line clearing and cleaning procedures. In fact, multiple food products can be processed simultaneously. Furthermore, the invention provides unique treatment conditions which operate both at target temperature and under saturated steam pressure to minimize or eliminate undesirable water loss which would affect the quality of the products.

The temperature and pressure remain constant with a balance of steam flowing into and out of the chamber to attain and maintain uniform treatment temperature and saturated steam conditions, protecting the quality of the products.

According to another aspect of the invention, the saturated steam within the bioburden reduction chamber is agitated to increase permeation into the material being treated. Any means of moving the saturated steam within the chamber can be used. For example, a blower can be used to distribute the saturated steam evenly throughout the bioburden reduction chamber.

According to yet another aspect of the invention, large chambers ranging in size from, for example, about 100 $ft^3$ to about 8000 $ft^3$ or small chambers ranging in size from, for example, about 1 $ft^3$ to about 100 $ft^3$ may be employed.

Preferably, the pressure within the bioburden reduction chamber is maintained at pressure between about 0.1 psia and 14.7 psia.

The present invention is also directed to treated consumer products that result from use of the present inventive method and apparatus.

Additional objects and attendant advantages of the present invention will be set forth in the description and examples that follow, or may be learned from practicing the method or using the apparatus of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

BRIEF DESCRIPTION OF THE DRAWINGS

FIG. 2 demonstrates the process as originally disclosed. Portions of the load (Tmax) reach T1 very quickly after the steam is injected. Other portions of the load (Tmin) tend to remain cool for a long time and then suddenly rise towards T1. This is acceptable for many products. For those products that are temperature sensitive over extended periods, FIG. 3 shows the alternative within the present disclosure. The maximum temperature achieves T1a rapidly while the minimum temperature lags behind. Once there is convergence between the two trends, steam is injected to P2 which rapidly raises both the minimum and maximum temperature to T1.

In the following description, like parts are designated by like reference numerals throughout the figures.

DETAILED DESCRIPTION OF THE INVENTION

All patents, patent applications and literatures that may be cited herein are incorporated herein by reference.

Figure 1:
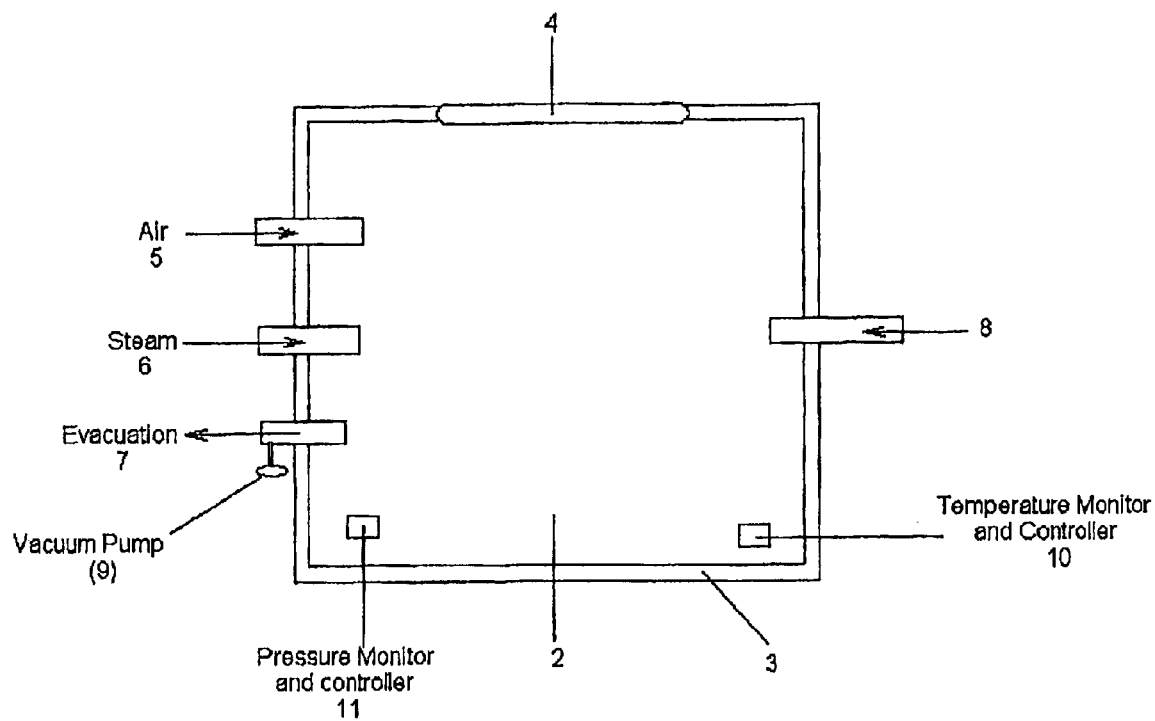
FIG. 1 is a schematic showing one example of an apparatus for using a continuous flow of saturated steam to reduce bioburden in accordance with the method of the invention.
Figure 2:
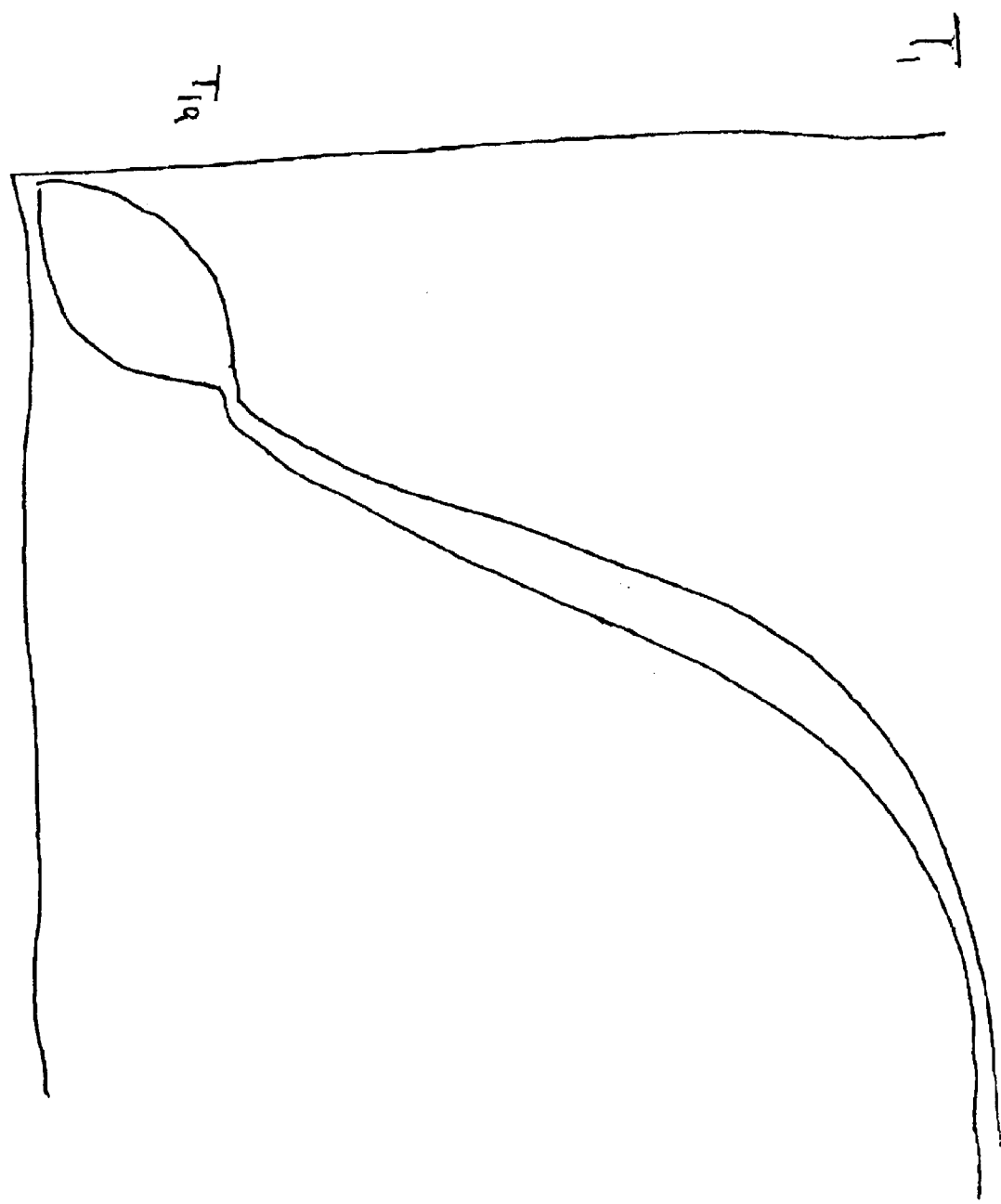
FIGS. 2 and 3 show temperature on the Y axis against time on the X axis. They show the process beginning with the first steam inject through the end of the sterilization phase.
Figure 3:
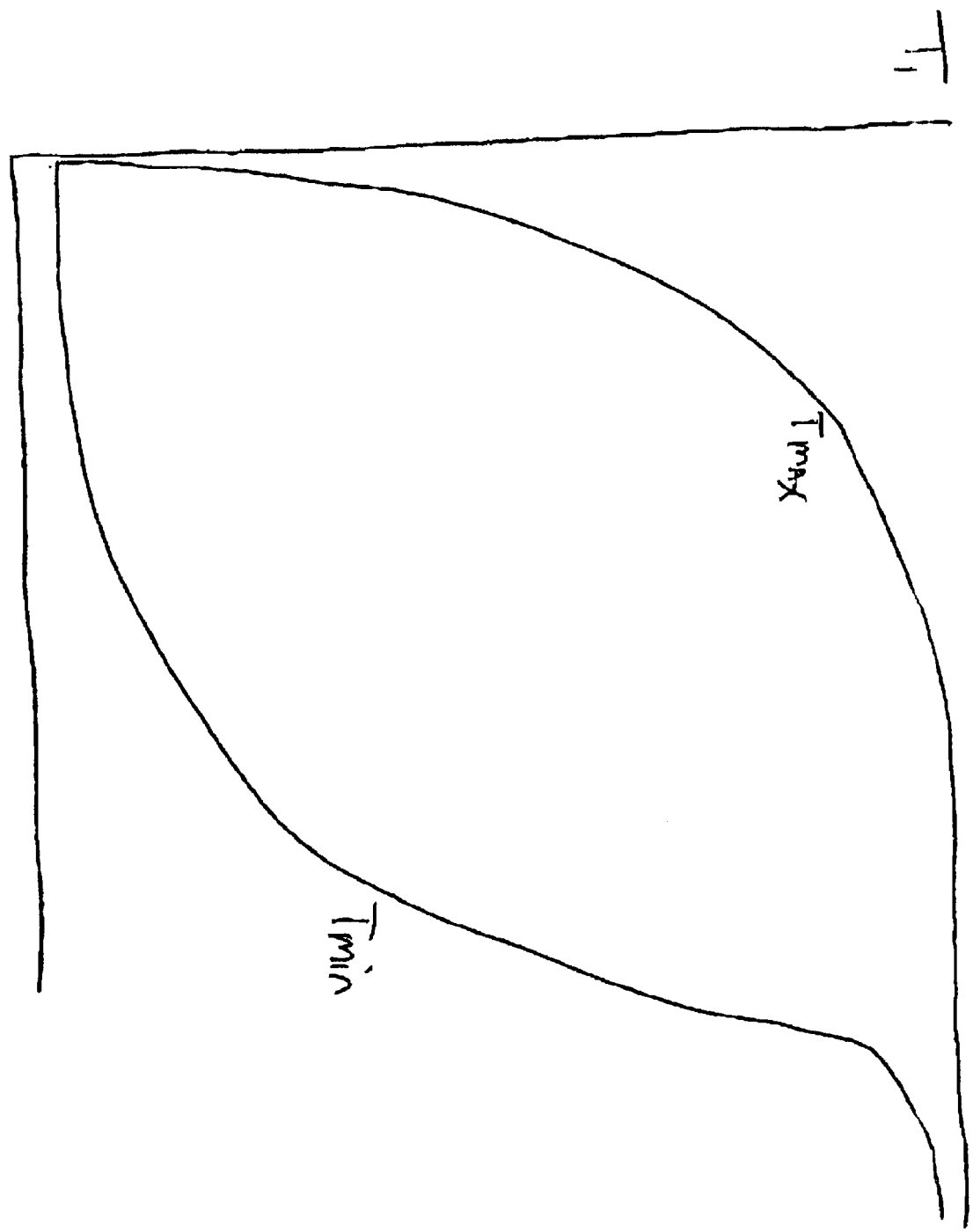

Referring to FIG. 1, a product to be treated is placed on pallets and loaded into a treatment vessel 1. The treatment vessel 1 is a steel chamber 2 with temperature control provided by temperature monitor and controller 10 and heating jackets 3 that surround the exterior of the chamber 2 and pressure control provided by pressure monitor and controller 11. The chamber 2 is equipped with a door 4, which, when shut, the chamber 2 can be described as vacuum tight. The chamber 2 is equipped with air injection system 5, steam injection system 6 and evacuation system 7. It may also be equipped with an inert gas injection system 8. The apparatus includes improvements that are incorporated into the invention.

Prior to initiating the method, a desired treatment temperature is selected. For example, in many cases effective bacterial decontamination can be achieved by elevating product temperature above 160° F. (71.11° C.). Whereas the viability of noxious weed seeds can often be reduced at 212° F. (100° C.). Insects have varying ability to withstand elevated temperatures, as well. Based on selected temperature, a pressure is determined from the Saturated Steam Tables (CRC Handbook of Physics and Chemistry). In this example a pressure of 5.3361 PSIA would provide a saturated steam temperature of 165° F. (73.89° C.). This temperature exceeds the target temperature and ensures that the entire product load achieves the target temperature. Using the temperature monitor and controller 10, the chamber jackets 3 are heated to approximately 10° F. (−12.22° C.) higher than the target temperature. The additional energy provided by the chamber jackets 3 superheats the environment and maintains steam quality. The process of the invention may occur in a range of about 0.1–14 PSIA.

Once the chamber door 4 has been sealed, turning on the vacuum pump 9 lowers the pressure. The pressure continues to drop to as low an absolute pressure below the target pressure as the system can attain. Steam is injected via the steam injection system 6 into the chamber 2 until the pressure monitor and controller 11 determines that the pressure is equal to the target pressure. The steam may be introduced continuously or in a pulsed fashion. Then the vacuum pump 9 is turned on again. A balance of steam flowing into the chamber and out of the chamber is created so that the pressure remains constant. Ideally, the flow into the vacuum system remains at a maximum for the entire phase. This rapid flow of steam minimizes boundary layers surrounding the product and assists in removing concentration of air from the chamber.

The process is self-limiting in that the temperature cannot exceed a known maximum and cannot fall below a known minimum. As the air concentration approaches 0%, the product and chamber temperatures will converge on the temperature dictated by the steam table. The maximum temperature that can be achieved in the product is equal to the heating jacket temperature and the minimum temperature that can be achieved is approximately the temperature dictated by the saturated steam table at the chamber pressure. This resolves the issues of overheating portions of a load in an effort to achieve the minimum temperature in another region.

Once the target temperature has been achieved, the process continues for a predetermined period of time. For example, the process may continue for 1–6 hours or more to ensure adequate lethality within the product load. Adequate lethality occurs when the target bioburden that are sensitive to the pre-selected temperature have been killed. By using the process of the invention, one can select a temperature sufficiently low to protect the product but sufficiently high to kill the target bioburden. For example, many spices can be safely heated at 170° F. (76.67° C.) to treat for salmonella, which is killed at 160° F. (71.11° C.).

Following the dwell period, the product is cooled and dried. Cooling is carried out in accordance with conventional methods. For example, the chamber may be flushed with multiple inert gas washes via the inert gas ejection system 8. Nitrogen heated to the chamber target temperature may be added to the chamber until the pressure is at or above atmospheric pressure. The vacuum pump 9 is turned on and the pressure is reduced to the minimum pressure attainable in the system. This nitrogen pulse followed by re-evacuation is repeated until the produce temperature stops falling. Product temperature decreases as subsequent washes remove water from the product load. As the water evaporates the load cools. Maintaining the heating jackets 3 on the chamber 2 at the elevated temperature ensures that condensation does not occur and that steam removal occurs as efficiently as possible. At this time, air is introduced into the chamber and the process is complete.

According to another embodiment, the process begins with an initial evacuation. Steam to a pressure P1a lower than the final target pressure is introduced. The steam flows or is pulsed at this pressure until the product temperature is uniformly heated to T1a and the air is removed from the chamber. The steam is injected to pressure P1 and the temperature rises to T1, the target pressure and temperature, for the process as previously described, where it is dwelled. The process proceeds as described above.

This process is a suitable alternative for products which cannot stand exposure to elevated temperatures for extended periods. By introducing a dwell early in the process at a lower temperature and pressure, the product is pre-heated to a "safe" temperature and the air from the load is completely displaced. The saturated steam environment provides a better media to transfer heat upon the introduction of steam from P1a to P1. The product is thus warmed, the air is eliminated and the product is moistened. Steam is then injected to the higher pressure and the temperature through the load rises quickly.

The present invention will be further illustrated by the following non-limiting examples:

EXAMPLE

Almonds were intentionally inoculated with a nonpathogenic strain of listeria. The almonds were then treated with saturated stem in accordance with the method of the invention. Controls were inoculated but not treated. Almonds were either whole nutmeats without the shell or chopped nutmeats.

| | |
|---|---|
| Treatment Time: | 6 hours |
| Chamber Temperature: | 150° F. (65.56° C.) +/− 5° F. (−15° C.) |
| Absolute Pressure in Chamber: | 5.3361 PSIA |

The above data represents the process used to treat the almond samples. The variables above may be changed in accordance with the invention.

Results

After treatment, the almonds were tested for the presence of listeria using well-known detection techniques.

| Inactivation of Listeria on Inoculated Almonds | | | |
|---|---|---|---|
| Experiment | Nutmeats | Listeria/Gram (Control) | Listeria/Gram (Treated) |
| 1 | Chopped | $2 \times 10^6$ | ND |
| 2 | whole | $2 \times 10^6$ | ND |

[1]ND = not decided

EXAMPLE

Niger seed imported from Myanmar and India as feed for finches, is contaminated with noxious weeds not indigenous to the United States, including dodder (Cuscuta spp.). In addition to dodder, these weeds may include, *Cuscuta japonica, Asphodelus fistulosus, Borreria alata, Commelina benghalensis, Impomea triloba, Ischaemum rugosum*, Oryza sp. (red rice), *Paspalum scrobiculatum, Setaria pallidefusca* and *Urochloa panicoidea*, Eleusine spp., Seteria spp., Pennisetum spp., Panicum spp., Echinochloa spp., Sorghum spp., *Zea mays*, and Oryza spp.

| | |
|---|---|
| P1a | 2.0 PSIA |
| T1a | 150° F. (65.56° C.) |
| P1 | 14.5 PSIA |
| T1 | 215° F. (101.67° C.) |

After treatment by the method of the invention, the germination rate of these contaminating seeds was 0%.

Various other modifications will be apparent to and can be readily made by those skilled in the art without departing from the scope and spirit of this invention. Accordingly, it is not intended that the scope of the invention be limited to the description as set forth herein, but rather that the invention be broadly construed.

What is claimed is:

1. A method for reducing bioburden, comprising:
   a. placing a material to be treated into a chamber;
   b. selecting a desired temperature $T1$, wherein said desired temperature $T1$ is based on the material being treated;
   c. determining a target sub-atmospheric pressure $P1$, wherein said target pressure $P1$ provides a saturated steam environment in said chamber at said desired temperature $T1$;
   d. creating a vacuum in said chamber;
   e. introducing steam into said chamber until said target sub-atmospheric pressure $P1$ is achieved, thus indicating that said chamber has reached said target temperature $T1$ and saturated steam is present in the chamber; and
   f. maintaining the chamber at substantially said temperature $T1$ and pressure $P1$ for a period of time sufficient for bioburden reduction.

2. The method of claim 1, wherein said steam flows into and out of said chamber substantially continuously.

3. The method of claim 1, wherein said sub-atmospheric pressure $P1$ is between about 0.1–14 PSIA.

4. The method of claim 1, further comprising after step d:
   d.(1). introducing steam at a pressure $P1a$, which is lower than $P1$, until the temperature is uniformly heated to a temperature $T1a$.

5. An apparatus for bioburden reduction, comprising:
   a. a bioburden reduction chamber;
   b. a temperature monitor and controller, wherein said temperature monitor and controller permit a desired temperature $T1$ to be achieved in said chamber;
   c. a pressure monitor and controller, wherein said pressure monitor and controller calculate a sub-atmospheric pressure $P1$ capable of achieving a saturated steam environment in said chamber based on said desired temperature $T1$;
   d. a steam injection system; and
   e. an evacuation system.

6. The method of claim 1, wherein the material comprises one or more objects that are the same or different.

7. The method of claim 1, wherein the saturated steam in the chamber is agitated.

8. The method of claim 1, wherein the period of time sufficient for bioburden reduction is from about 1 to about 6 hours.

9. A material treated by the method of claim 1, having a reduced bioburden.

10. A system comprising:
    a. a bioburden reduction chamber;
    b. a temperature monitor and controller, wherein said temperature monitor and controller permit a desired temperature $T1$ to be achieved in said chamber;
    c. a pressure monitor and controller, wherein said pressure monitor and controller calculate a sub-atmospheric pressure $P1$ capable of achieving a saturated steam environment in said chamber based on said desired temperature $T1$;
    d. a steam injection system; and
    e. an evacuation system.

* * * * *